US00PP08463P

United States Patent [19]

Bianco

[11] Patent Number: Plant 8,463

[45] Date of Patent: Nov. 16, 1993

[54] GRAPEVINE CV. BIANCO ONE

[75] Inventor: Robert O. Bianco, Indian Wells, Calif.

[73] Assignee: Anthony Vineyards, Inc., Bakersfield, Calif.

[21] Appl. No.: 964,041

[22] Filed: Oct. 20, 1992

[51] Int. Cl.[5] ..... A01H 5/00

[52] U.S. Cl. ..... Plt./47.1

[58] Field of Search ..... Plt./47.1

[56] References Cited

U.S. PATENT DOCUMENTS

Plt. 5,833 12/1986 Gargiulo ..... Plt. 47.1

*Primary Examiner*—James R. Feyrer
*Assistant Examiner*—Erich E. Veitenheimer
*Attorney, Agent, or Firm*—Synnestvedt & Lechner

[57] ABSTRACT

A grapvine cv. Bianco One that is a mutation of the Flame Seedless grapevine and that is particularly characterized by its round berries which have a bright red skin color, very crisp flesh texture, high sugar content, excellent eating quality, and which ripen approximately 15 days before Flame Seedless and differ from Flame Seedless in having a somewhat smaller berry size, smaller vestigial seeds and earlier time of flowering.

3 Drawing Sheets

This invention relates to the discovery and asexual propagation of a new variety of hybrid grapevine *Vitis vinifera* cv. Bianco One. The Bianco One variety bears bright red seedless berries that have a pleasing taste and other desirable table grape characteristics. The Bianco One variety was discovered by Robert O. Bianco as a whole vine mutation of a Flame Seedless (an unpatented variety) growing in a commercial vineyard near Mecca, Riverside County, Calif. Robert O. Bianco asexually propagated the new variety from a hardwood cutting taken from the mutation and demonstrated its stability. The Bianco One grapevine maintains its distinguishing characteristics as hereinafter set out through successive asexual propagations.

The new Bianco One variety may be distinguished from its parent Flame Seedless and also from other presently available commercial cultivars by the following combination of characteristics: it can be distinguished from the Flame Seedless variety which it most nearly resembles by its substantially earlier ripening period, earlier date of bloom, smaller vestigial seed size and smaller berry size. The new grape vine variety can be distinguished from the Perlette variety by its earlier ripening (5 to 6 days) period and its red skin color. It can be distinguished from two other red seedless grapes commercially grown in Califorina, the Crimson variety and the Emperatriz (U.S. Plant Pat. No. 5,833) variety, by its earlier ripening (approximately three months eariler) and by having a round rather than elongated berry shape.

In the accompanying drawings.

Figure 1:
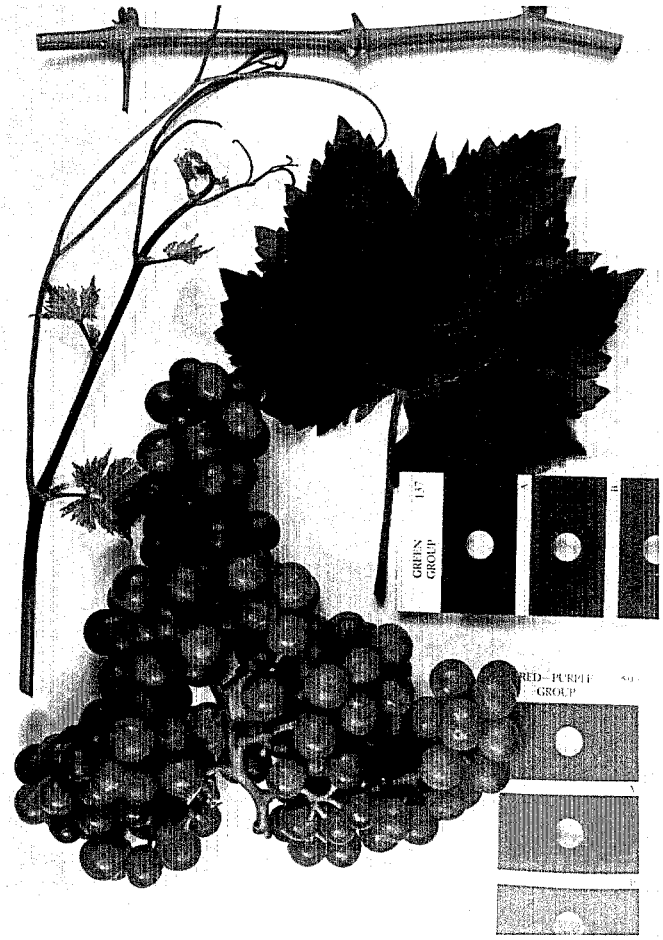
FIG. 1 illustrates, in full color, a typical cluster of berries, stem section, young shoot and mature leaf blade of the new Bianco One grapevine.
Figure 2:
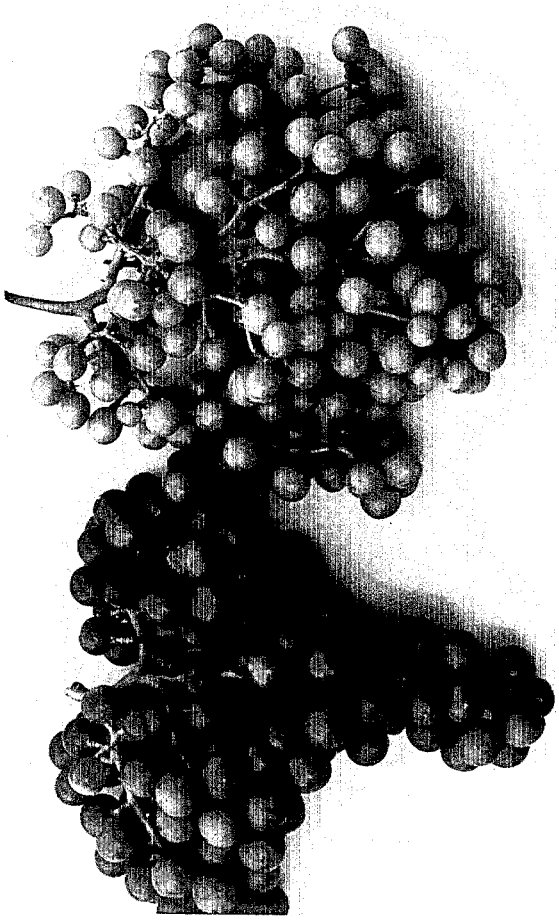
FIG. 2 illustrates a Bianco One variety berry cluster with color (on left) and a Flame Seedless variety berry cluster without color (on right) picked on the same date, showing that Bianco One ripens eariler than Flame Seedless.
Figure 3:
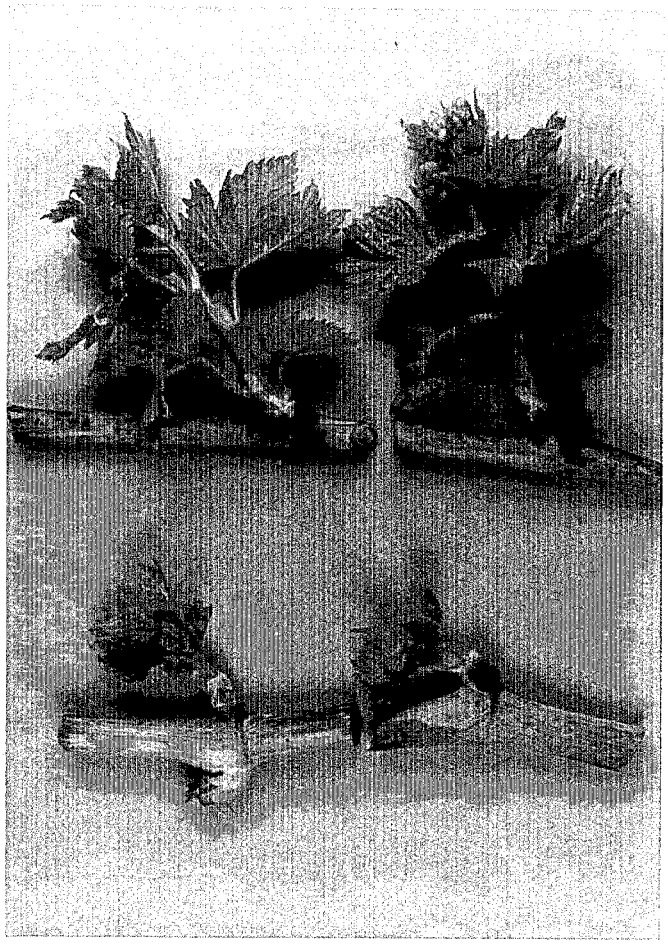
FIG. 3 illustrates Bianco One (top) and Flame Seedless (bottom) photographed just after bud break in the spring, showing that Bianco One breaks bud and commences growth eariler than Flame Seedless.

Throughout this application, color names beginning with a small letter signify that the name of the color, as used in common speech, is aptly descriptive. Color names beginning with capital letters designate values based on The R.H.S. Colour Chart of The Royal Horticultural Society of London, England.

The descriptive matter which follows pertains to grapevines of the new Bianco One variety grown near Mecca, Riverside County, Calif., in 1992, and is believed to apply to plants of the variety grown under similar conditions of soil and climate elsewhere.

VINE

The vine on its own root is small in size and of medium vigor. The foliage is of open density. The vines are hardy, productive, bearing their fruit regularly.

The trunk is of medium thickness and bears short, split straps. The surface is of medium texture and about Greyed-Orange 165B in color. The canes are average in caliper and are of smooth surface texture. Canes usually are about 245 cm. long and have a diameter of about 1.5 cm. at the node. Nodes are rounded and of medium length. The average distance between nodes is about 8.7 cm.

SHOOTS

Shoots exhibit weak vigor during flowering. Flowering shoots are semi-erect when not tied. The dorsal sides of both the internodes and nodes, and the ventral side of the nodes are green with red stripes, about Greyed Purple 183B in color. The ventral side of the internodes is green, about Green 143C in color. Anthocyanin coloration is absent from or very weak in the immature shoot buds.

Young shoot tips are half-open in form. Weak anthocyanin coloration is distributed as piping at the edges of the young shoot tips. Neither prostrate nor erect hairs are present at the shoot tips.

Woody shoots are circular in cross section. The surface of woody shoots is smooth and yellowish brown, about Greyed-Orange 165B in color.

Lenticels are absent. No erect hairs are present at either the nodes or internodes.

Tendrils, averaging about 26.5 cm. in length and of medium thickness are discontinuously distributed on the shoot at full flower. Tendrils are about Yellow-Green 145A in color. Tendrils are trifurcated in form.

Leaf producing buds of which there are many, are slightly pointed and of medium size — about 6.4 cm. Buds are slightly held out at an angle of about 45°. Basal buds are most fruitful and seldom dead.

LEAVES

In general, the upper surface of a young leaf is about Yellow-Green 144A in color. Prior to flowering anthocyanin is of medium intensity in the distal leaves. On the lower surface of the young leaves, both prostrate and erect hairs are very sparsely distributed between veins and very sparsely on the veins.

Mature leaves have a generally circular outline and an involute profile. Leaves are of average size (about 14.7 cm. long and about 20.5 cm. wide) and the blades are of medium size, pentagonal in shape and have 5 lobes. The leaf blade tip lies in the plane of the leaf. The leaf margin shows medium undulation. The leaf apex is cuspidate; the leaf base is U-shaped. The leaf blade has undulations between the main and lateral veins but only near the petiole. Teeth are convex on both sides. The upper leaf sinuses have slightly overlapping lobes.

The upper surface of the leaf is near Yellow-Green 137A in color. Anthocyanin coloration is of average intensity on the main veins of the upper leaf surface. The upper leaf surface is smooth in texture, of average glossiness and has a semi-glossy surface appearance; pubescence is absent. Blistering on upper side surface of blade is absent or very weak. There is no goffering of the blades.

The lower leaf surface is about Green 137C in color, weak in glossiness and with no pubescence. Anthocyanin coloration of the main veins on the lower leaf surface is weak. The lower leaf surface is smooth in texture and semi-glossy in surface appearance.

The petiole is about 11.1 cm. in length and shorter than the middle vein. There are no erect hairs present on the petiole. The petiole sinus is slightly open and U-shaped at the base. There are no particularly distinguishing features with respect to the petiole sinus. The lobes forming the upper leaf sinus are slightly overlapping. The base of the upper leaf sinus is U-shaped.

Stiples are persistent.

FLOWERS

During the 1992 growing season in Mecca, Riverside County, Calif., Bianco One flowers attained full bloom on Mar. 16, as compared to Mar. 23 for Flame Seedless, slightly earlier than most other similar varieties growing in this area. Usually two (2) flower clusters are borne per shoot, and the duration of bloom is short, about 5 days. Flowers are fertile and hermaphroditic.

FRUIT

The fruit of the new variety ripens very early, about 15 days ahead of the Flame Seedless variety. On May 7, 1992 Bianco One had 15.0 brix sugar and 0.56 grams/100 ml acid as compared to 10.0 brix sugar and 1.56 grams/100 ml acid for Flame Seedless.

The fruit has excellent eating quality, is suitable for market use and has average keeping quality and good shipping qualities; it has average resistance to insects and diseases.

The size of the berry clusters (excluding the peduncle) is average, weighing on the average about 382 grams. The compact, conical cluster usually bears an average of about 142 berries.

The peduncle is of short length and shows weak lignification. Peduncle color is near Yellow-Green 145B.

Berries are small (0.98±0.22 grams naturally and 3.5 grams when treated with gibberellic acid), uniform in size and are of oblate, slightly flat shape with a circular cross section (on average the longitudinal axis is about 16.5 mm long, and the horizontal axis is about 17.5 mm in diameter when treated with gibberellic acid). The brush usually pulls out of the berry without the pedicel. The seeds are very small and not noticeable when eaten. Berries are near Red-Purple 59A in color. When ripe, the berries have a high sugar content, a mild subacidic taste and neutral flavor.

The skin is of average thickness, is tenacious to the flesh, without roughness and reticulation is present. The flesh is very crisp in texture.

What is claimed is:

1. A new variety of gravevine cv. Bianco One, substantially as herein shown and described.

* * * * *